(12) United States Patent
Keller

(10) Patent No.: US 8,074,843 B2
(45) Date of Patent: Dec. 13, 2011

(54) TWO-PART DOUBLE SYRINGE

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 517 days.

(21) Appl. No.: 12/224,386

(22) PCT Filed: Feb. 27, 2007

(86) PCT No.: PCT/CH2007/000095
§ 371 (c)(1),
(2), (4) Date: Aug. 26, 2008

(87) PCT Pub. No.: WO2007/098624
PCT Pub. Date: Sep. 7, 2007

(65) Prior Publication Data
US 2009/0134186 A1    May 28, 2009

(30) Foreign Application Priority Data

Mar. 1, 2006 (CH) .......................... 328/06

(51) Int. Cl.
*B67D 7/70* (2010.01)
*B65D 88/54* (2006.01)
(52) U.S. Cl. ..................... 222/137; 222/145.6; 222/327; 222/386
(58) Field of Classification Search .................. 222/137, 222/135, 386, 145.1, 145.5, 145.6, 325, 326, 222/327
See application file for complete search history.

(56) References Cited

U.S. PATENT DOCUMENTS

| 4,979,942 A | 12/1990 | Wolf et al. |
|---|---|---|
| 5,082,147 A * | 1/1992 | Jacobs ........................... 222/137 |
| 5,104,005 A * | 4/1992 | Schneider et al. ............. 222/137 |
| 5,249,709 A | 10/1993 | Duckworth et al. |
| 5,819,988 A * | 10/1998 | Sawhney et al. ............... 222/137 |
| 5,875,928 A * | 3/1999 | Muller et al. .................... 222/82 |
| 6,352,177 B1 * | 3/2002 | Bublewitz et al. ............... 222/82 |
| 6,394,314 B1 * | 5/2002 | Sawhney et al. ............... 222/137 |
| 6,458,095 B1 * | 10/2002 | Wirt et al. ........................ 604/82 |
| 6,732,887 B2 | 5/2004 | Bills |
| 6,824,016 B2 | 11/2004 | Muhlbauer et al. |
| 2003/0050597 A1 | 3/2003 | Dodge et al. |

FOREIGN PATENT DOCUMENTS

| EP | 0 521 434 | 1/1993 |
|---|---|---|
| EP | 0 730 913 | 9/1996 |

* cited by examiner

*Primary Examiner* — Kevin P Shaver
*Assistant Examiner* — Stephanie E Williams
(74) *Attorney, Agent, or Firm* — Foley & Lardner LLP

(57) ABSTRACT

A two-part double syringe or double cartridge having associated, isolated containers with respective outlets which are connected to each other by a connecting element, the connecting element forming a unit that includes a holder with two container receptacles, a support wall, and a one-piece retaining flange, the support wall having recesses for receiving the container outlets and the container receptacles having respective guiding sleeves, and the outlet side being configured as a fastening area for the attachment of a mixer or accessory. Such a double syringe allows the containers to be filled separately, is very solid, and can be operated like a one-piece double syringe.

11 Claims, 4 Drawing Sheets

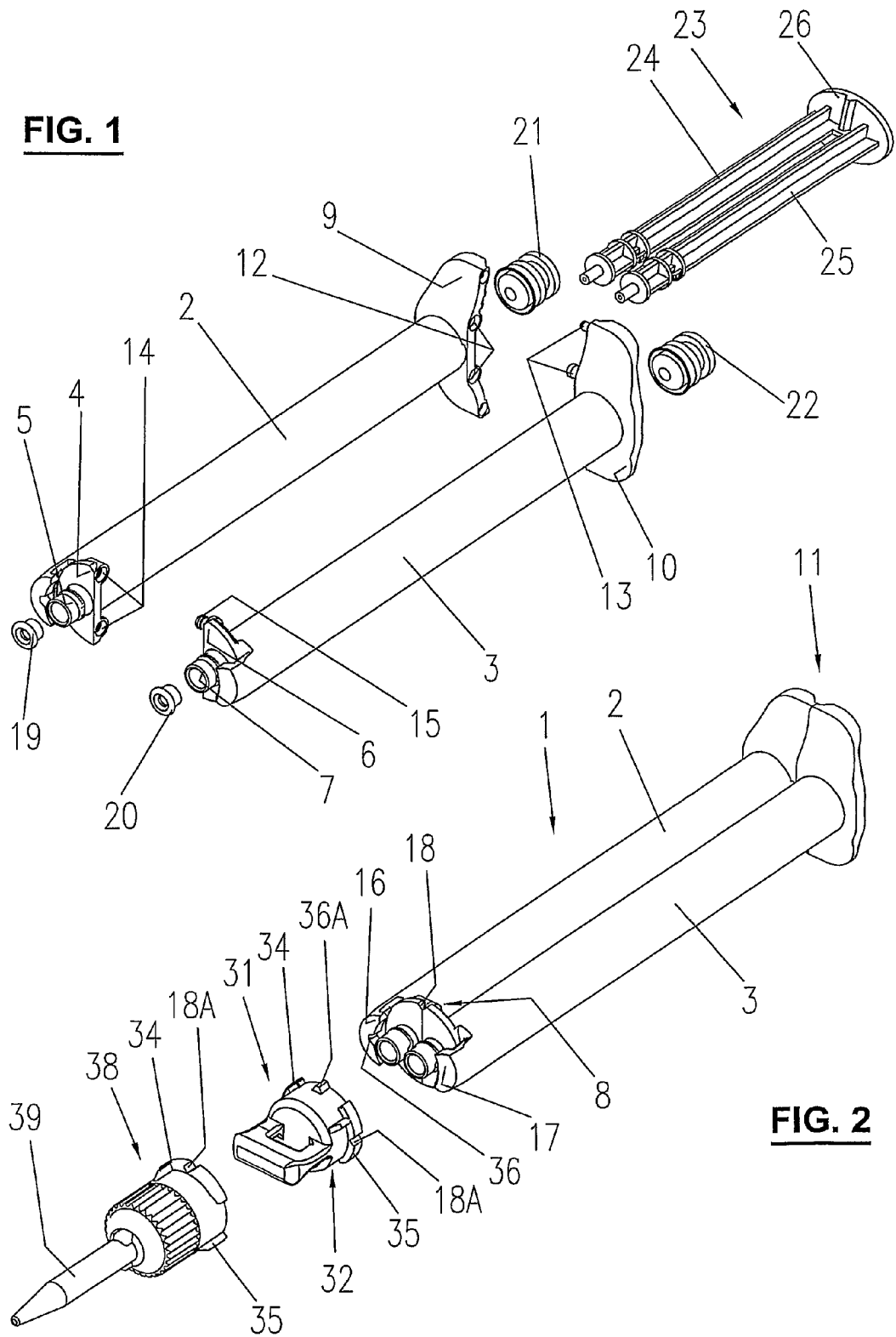

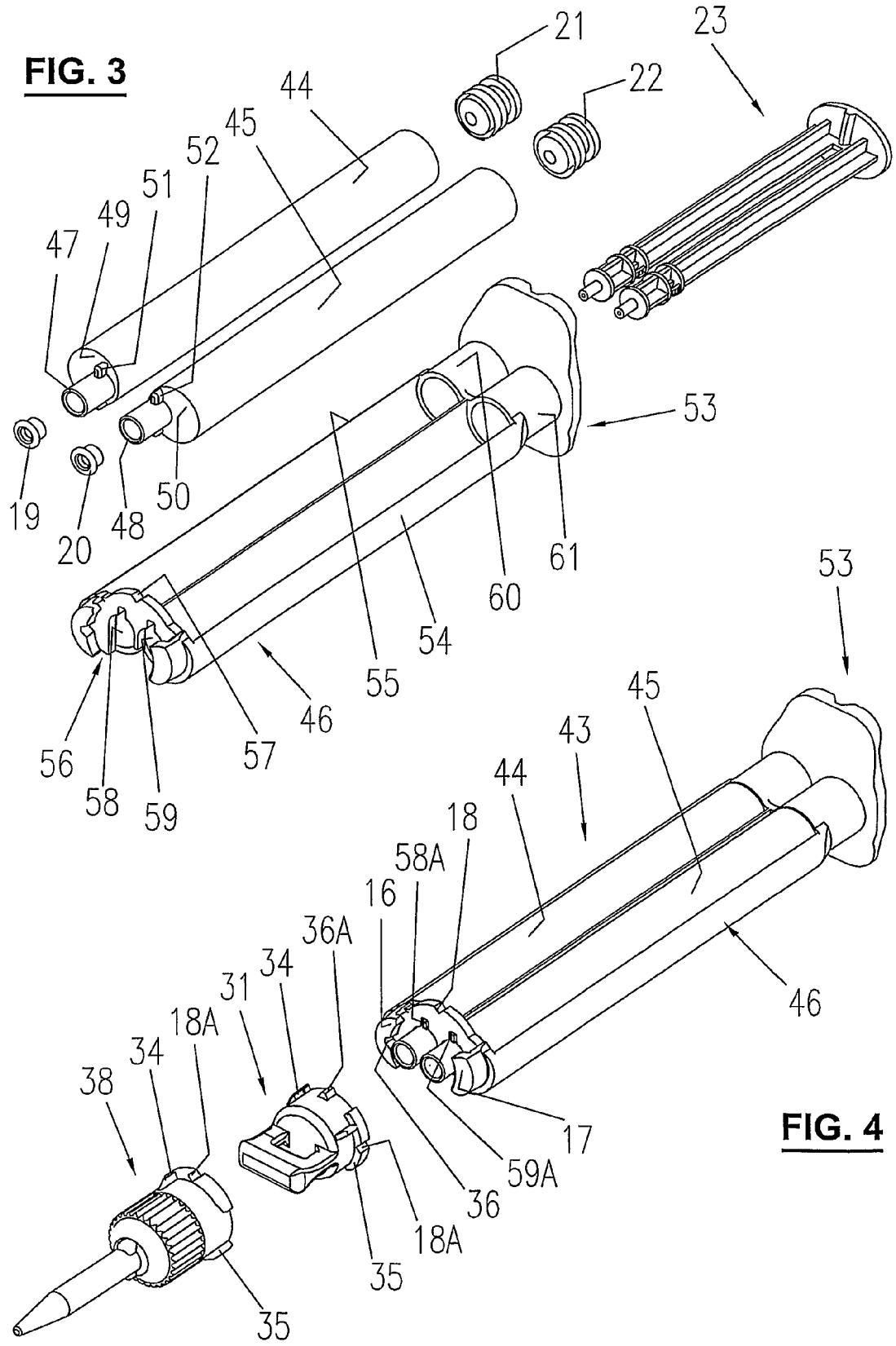

US 8,074,843 B2

TWO-PART DOUBLE SYRINGE

This application is the National Phase of PCT/CH2007/000095, filed Feb. 27, 2007, which claims priority to Switzerland Patent Application No. 328/06, filed Mar. 1, 2006. The contents of the foregoing applications are incorporated by reference in their entirety.

FIELD OF INVENTION

The present invention relates to a two-part double syringe or double cartridge having associated containers with respective outlets, of which at least one is isolated and connected to the other container by connecting means, according to the preamble of claim 1. Such a two-part cartridge is e.g. known from U.S. Pat. No. 6,732,887B2. The double syringe disclosed in this patent specification has transparent containers of differing colors and is intended to receive an applicator syringe that may also comprise a mixing helix. If different accessories are to be attached to the double syringe, e.g. a closure or a mixer or other applicator parts, different connectors are required.

Generally, two-component products are stored in double syringes respectively double cartridges and mixed by means of a directly attached static mixer. Such one-piece double syringes are produced in a plastic injection mold, and the two containers are therefore not separable from each other. This means that both containers consist of the same material. For certain two-component materials, this may be a disadvantage as the two components may possibly be incompatible with the plastic material of the double syringe or cartridge, thereby resulting in dissimilar requirements with respect to the syringe material. Thus, for example, a polypropylene container may be ideal for one component while the other component may require a container of polyamide.

Furthermore, in the medical field, there is a need to fill the containers for the two components separately and to subject them to different subsequent treatments, e.g. different sterilization processes, a sterile or non-sterile filling procedure, etc.

PRIOR ART

Theoretically it is possible to use two standard single syringes and to connect the syringe bodies and the plungers, respectively. To dispense them, the two components are delivered to the static mixer by means of a special Y piece. This is e.g. realized in U.S. Pat. No. 4,979,942.

It is already an improvement over such connected single syringes with a Y piece to use a double syringe composed of single containers that can be filled and processed separately. A double syringe of this kind is described in the introduction.

Among a large number of other two-part syringes, U.S. Pat. No. 6,824,016 shall be mentioned which includes connecting elements for coupling two containers while the outlet of one of the containers is pushed into an opening in the stop plate of the second container.

Furthermore, US 2003/050597 A1 discloses a dispensing appliance having a holder into which individual containers can be loaded, the patent application being directed to the process of filling the containers and the latter being pushed from the inlet side into a retaining flange on the container.

SUMMARY OF THE INVENTION

On the background of this prior art, it is the object of the present invention to provide a two-part syringe, more particularly a double syringe, that is rugged and torsionally rigid and able to receive a large number of conventional accessories without requiring adapter elements. This is accomplished by a two-part syringe wherein the connecting means comprise a unit consisting of at least a container receptacle, a support wall, and a retaining flange, the support wall having at least one recess for receiving at least one of the container outlets and each container receptacle having a guiding sleeve, and the outlet side being configured as a fastening area for the attachment of a mixer or accessory.

BRIEF DESCRIPTION OF THE DRAWINGS

The invention will be explained in more detail hereinafter with reference to drawings of exemplary embodiments.

FIG. 1 shows a first exemplary embodiment of a disassembled syringe in a perspective view,
FIG. 2 shows the syringe of FIG. 1 when assembled,
FIG. 3 shows a second exemplary embodiment of a disassembled syringe,
FIG. 4 shows the syringe of FIG. 3 when assembled.

DETAILED DESCRIPTION OF PREFERRED EMBODIMENTS

Figure 5:
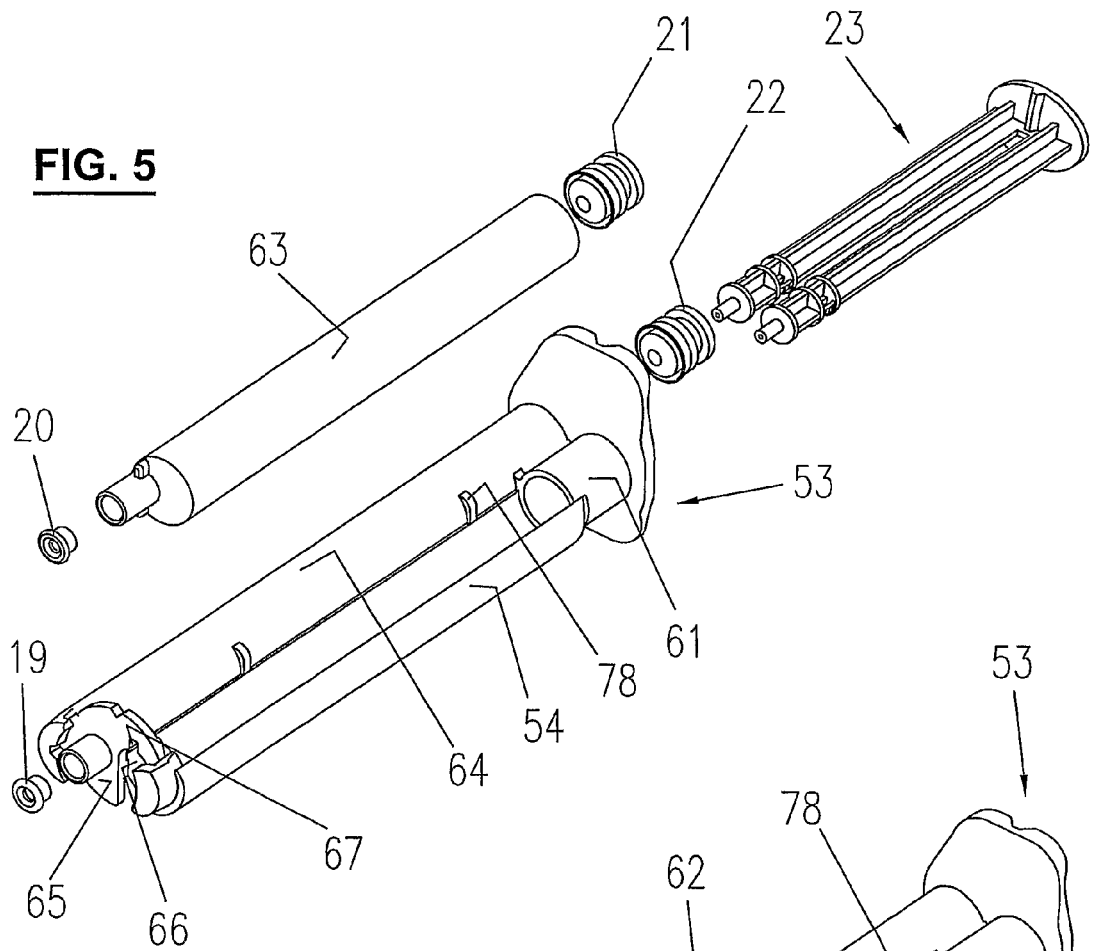
FIG. 5 shows a third exemplary embodiment of a disassembled syringe.

FIG. 1 shows in a first exemplary embodiment the two isolated containers 2 and 3 of double syringe 1, support wall portion 4 of container 2 having outlet 5 arranged thereon and support wall portion 6 of container 3 outlet 7. The two support wall portions together form support wall 8.

At the other end of the containers, on the inlet side, container 2 has a retaining portion 9 and container 3 a retaining portion 10 which together form retaining flange 11.

One of the containers, here container 2, is provided on its retaining portion 9 with snap openings 12 while retaining portion 10 of container 3 has corresponding connecting pins 13, and on its support wall 4 with snap openings 14 while support wall portion 6 has connecting pins 15. Alternatively, single connecting pins and snap openings may be provided. All in all, a stable connection is obtained due to the fact that the two containers are connected by their rigid portions, i.e. their support walls and flanges.

As appears in FIG. 2, support wall 8 is provided with a coded interface that is known per se and comprises, next to the spaced container outlets, two coded bayonet tabs 16 and 17 so that the same closures and mixers as used for conventional, one-piece double syringes or double cartridges can be connected if they have the matching, coded bayonet cams 34 and 35. In the present case, the bayonet members, respectively the distances between them, are different in width. In addition, further coding means that are known per se, such as coding means in the form of a nose 36A on the closure cap or on the mixer and a corresponding notch 36 in a bayonet tab, here in tab 16, as well as visual coding means such as a visual coding notch 18 in the support wall and a corresponding visual coding notch 18A in the closure cap or in the mixer are possible.

Instead of bayonet connectors, other coupling means of the accessories are possible, e.g. plug or snap connections that may also be coded. In this case, the coding may be achieved by means of different outlet diameters and/or by other coding means such as noses and notches.

In FIG. 1 it is suggested that the outlets may also be sealed by means of individual plugs 19 and 20 if the containers are filled separately. After the assembly of the double syringe, the outlets are secured by a closure cap 31, thereby increasing its cohesion. After removing the closure, a mixer 38 can be attached.

FIG. 1 further shows respective pistons 21 and 22 that are known per se. The pistons are actuated by a double plunger 23 which is manufactured in one piece and consists of two thrust rods 24 and 25 that are connected to each other by a thrust plate 26.

In the exemplary embodiment according to FIGS. 3 and 4, A double syringe 43 essentially comprises two cylindrical containers 44 and 45 which are received in a holder 46 that is rigid and receives the two cylinders on their entire length. FIG. 3 shows the two cylindrical containers 44 and 45 with respective outlets 47 and 48 whose diameter is smaller than that of the containers and which are located at the edge of front surfaces 49 and 50 of the containers. Near the outlets, the front surfaces have respective aligning noses 51 and 52. The other illustrated parts such as pistons 21 and 22 as well as double plunger 23 and the two plugs 19 and 20 are the same as in the preceding exemplary embodiment.

Holder 46 has a retaining flange 53 and at the other end of container receptacles 54 and 55 a support wall 56 on which front surfaces 49 and 50 of the containers come to rest. On its front side, the support wall has the same coded interface as in the preceding example with the two coded bayonet tabs 16 and 17 and a visual coding notch 18 as well as on its underside two recesses 58, 59 with incisions 58A and 59A for receiving the outlets with aligning noses 51 and 52, thereby allowing the containers to be inserted into the receptacles in a defined orientation and rotationally locked. At the end of the holder on the side of the retaining flange, the two container receptacles form respective guiding sleeves 60 and 61 which provide a precise guidance of the double plunger.

The other illustrated parts such as closure cap 31 and mixer 38 are the same as before. The double syringe is assembled by inserting the containers sealed by plugs 19 and 20 into the container receptacles and securing the plugs by means of closure cap 31.

Figure 6:
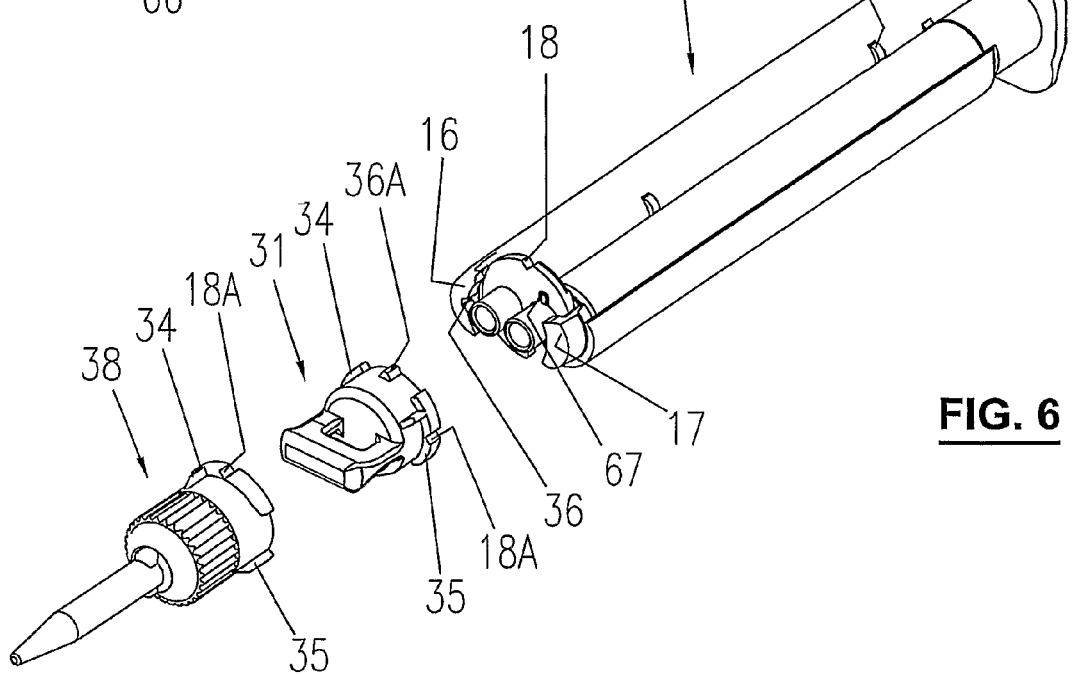
FIG. 6 shows the syringe of FIG. 5 when assembled.

The design of syringe 62 according to FIGS. 5 and 6 is similar to that according to FIGS. 3 and 4. However, first container 64 forms a unit together with retaining flange 53 and support wall 65 and container receptacle 54 while second container 63 is the same as container 45. Support wall 65 has a recess 66 with an incision 67 for receiving the outlet and the aligning nose of second container 63. Container 64 has cams 78 for holding down the second container. The remaining parts are the same as previously described.

Figure 7:
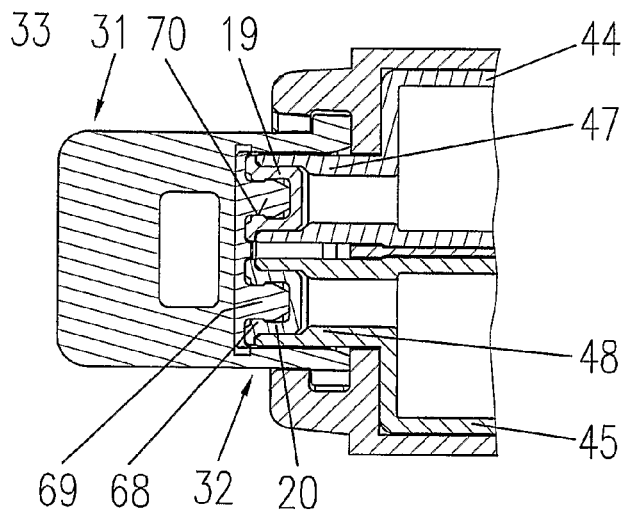
FIG. 7 shows the outlet area of a double syringe in a sectional view.
Figure 8:
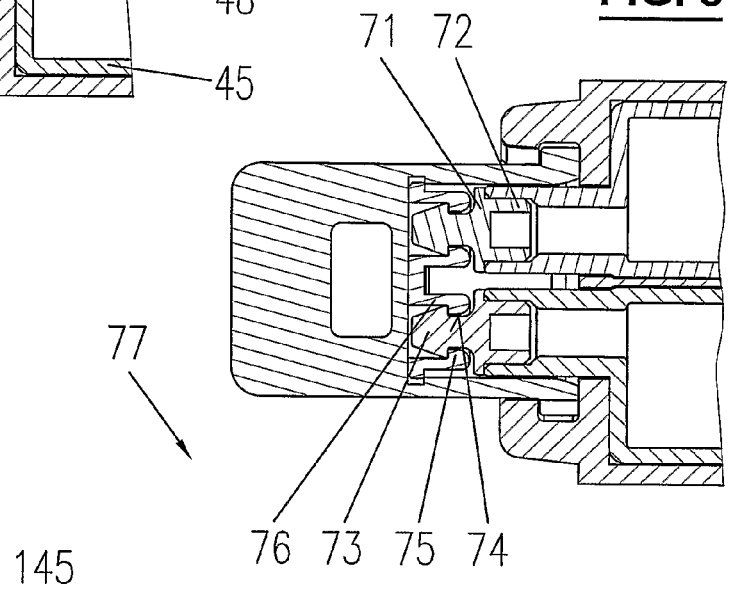
FIG. 8 shows an embodiment variant of the outlet area of a double syringe.

In FIGS. 7 and 8, two variants of a closure with individual plugs are illustrated, each sectional view showing the outlet area of the assembled and closed A double syringe of FIG. 4.

In FIG. 7, the outlet side end of containers 44 and 45 and of container receptacles 54 and 55 is illustrated. Both containers are sealed by plugs 19 and 20 while it is apparent in the enlarged view of FIG. 7 that the plugs each have an inner bulge 68. The two pegs 69 of closure cap 31 have corresponding grooves 70 such that the pegs snap into the plugs. This allows filling and closing the two containers independently of each other. When the closure cap is removed, both plugs are withdrawn simultaneously to allow the subsequent attachment of the mixer or of another accessory to the double syringe. The closure cap is retained by bayonet cams 34 and 35 in bayonet tabs 16 and 17 of the A double syringe.

In the embodiment variant according to FIG. 8, the plugs in the outlets have a gripping portion 73 in the form of a peg having a circumferential groove 74 in which the constricted end 75 of snap ring 76 engages which is rotatably arranged in closure cap 77. The function is the same as in the preceding example, i.e. both plugs 71 are simultaneously removed when the closure cap is withdrawn.

The exemplary embodiments according to FIGS. 1 to 8 have in common that the assembled syringe has a fastening area with a bayonet coupling portion that cooperates with the fastening area and bayonet coupling portion of the mixer or accessory.

Figure 9:
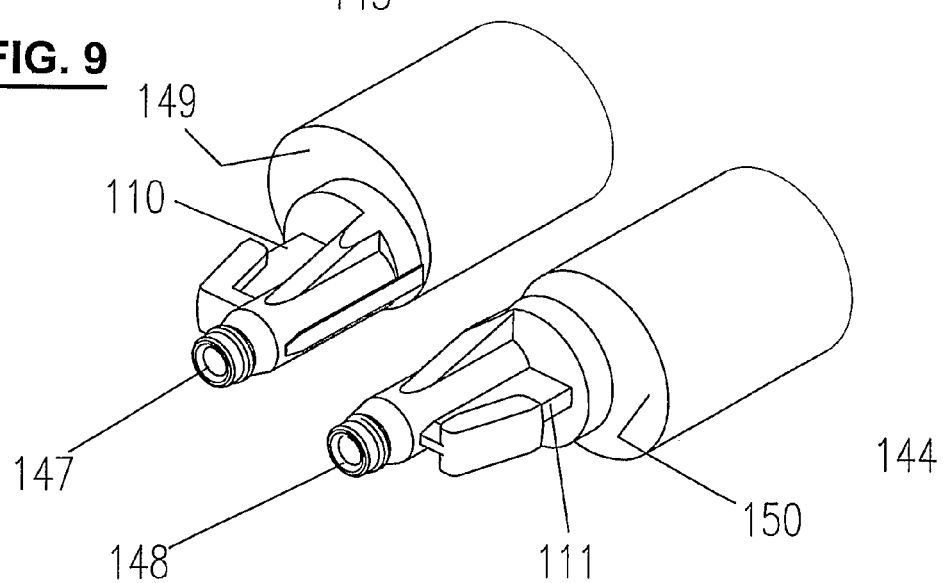
FIG. 9 shows a variant of the exemplary embodiment according to FIG. 3.

In contrast to the first series of exemplary embodiments, the fastening area of the syringe according to FIG. 9 is so designed that the mixer or accessory can be snap-fitted thereon and removed through a deformation of the fastening area of the mixer or accessory. In the variant according to FIG. 9 the fastening area of the syringe includes snap noses instead of bayonet coupling means, which cooperates with a respective fastening area at the accessory part.

FIG. 9 shows the two cylindrical containers 144 and 145 with respective outlets 147 and 148 whose diameter is smaller than that of the containers and which are located at the edge of front surfaces 149 and 150 of the containers. The fastening area comprises snap means at the outlets 147, 148.

Each outlet has a respective ridge 110, 111 that tapers from the front surface toward the outlet end. Each ridge has a respective saddle portion 112, 113 that ends at a distance from the front surface, thus forming respective snap noses 114, 115 that snap into snap openings in mixer or accessory.

The two saddle portions 112 and 113 do not have the same configuration, i.e. in this example, saddle portion 112 has an end ridge 116 on its outlet side and saddle portion 113 has none. The presence or absence of end ridge 116 constitutes a coding means such that the accessory can only be attached in an unequivocal orientation. Perpendicularly to the plane defined by the ridges, clamping guides 117 are provided.

In analogy to the above disclosed variant, where the fastening area with the retaining noses is disposed to a half each on the separate containers, a same fastening area can be disposed in the embodiment according to the FIGS. 1 and 2 at the containers 2 and 3. Similarly can the fastening area with the retaining noses be disposed in the embodiment according to FIGS. 5 and 6 at the container 63, resp. at the outlet of container 64.

It follows that similar to the above said other fastening areas with other fastening means can be used also.

The invention claimed is:

1. A two-part double syringe or double cartridge, comprising:
   a first and second container that each include an outlet; and
   a connecting element that receives at least one of the first and second container, wherein the connecting element comprises:
      at least one container receptacle,
      a support wall including at least one recess for receiving at least one of the outlet of the first and second container,
      a retaining flange, and
      an outlet side adjacent to the support wall,
   wherein each of the at least one container receptacle includes a guiding sleeve,
   wherein the outlet side comprises a fastening area configured to attach to a mixer or accessory, and wherein the outlet of the first container is sealed by a first plug and the outlet of the second container is sealed by a second plug, wherein the first and second plug are secured by a closure cap, and wherein the first plug and the second plug are configured to be withdrawn simultaneously when the closure cap is removed.

2. The two-part double syringe or double cartridge of claim 1, wherein the connecting element further comprises a holder that includes two container receptacles, the support wall, and the retaining flange, and wherein the support wall includes a plurality of recesses for receiving the outlet of the first container and the outlet of the second container.

3. The two-part double syringe or double cartridge of claim 1, wherein the connecting element further comprises the first container or the second container, one of the at least one container receptacle, the support wall, and the retaining flange, wherein the support wall includes one of the at least one recess for receiving the outlet of the first or second container.

4. The two-part double syringe or double cartridge of claim 1, wherein the support wall further includes a first support wall portion and a second support wall portion and the retaining flange includes a first retaining flange portion and a second retaining flange portion, wherein the outlet of the first container and the outlet of the second container are arranged on the first and second support wall portions and an inlet side of the first container and an inlet side of the second container include the first and second retaining flange portions.

5. The two-part double syringe or double cartridge of claim 1, wherein the fastening area comprises bayonet tabs.

6. The two-part double syringe or double cartridge of claim 1, wherein the fastening area is configured such that the accessory that is to be attached is attachable without a rotational movement and removable by compressing a fastening area of the accessory.

7. The two-part double syringe or double cartridge of claim 1, wherein the fastening area includes retaining noses on the outlet of the first container and the outlet of the second container.

8. The two-part double syringe or double cartridge of claim 1, wherein the each of the at least one recess includes incisions for receiving aligning noses on the outlet of the first container and the outlet of the second container.

9. The two-part double syringe or double cartridge of claim 1, wherein the connecting element further comprises at least one snap opening in a support wall portion and a retaining flange portion of one of the first and second container and at least one connecting pin on a support wall portion and a retaining flange portion of the other of the first and second container.

10. The two-part double syringe or double cartridge of claim 1, wherein the fastening area comprises first coding elements which cooperate with second coding elements in a fastening area of the closure cap or of the mixer.

11. The two-part double syringe or double cartridge of claim 1, wherein the retaining flange is configured to facilitate driving liquid out of the two-part double syringe or double cartridge.

* * * * *